(12) United States Patent
Hampton

(10) Patent No.: US 6,848,453 B2
(45) Date of Patent: Feb. 1, 2005

(54) ORNAMENTAL AND UTILITARIAN TOOTHPICK EXTENSION

(75) Inventor: Christian Kite Hampton, Marina, CA (US)

(73) Assignee: Sound Starts, Inc., Aromas, CA (US)

( * ) Notice: Subject to any disclaimer, the term of this patent is extended or adjusted under 35 U.S.C. 154(b) by 0 days.

(21) Appl. No.: 10/441,431

(22) Filed: May 15, 2003

(65) Prior Publication Data
US 2004/0226575 A1 Nov. 18, 2004

(51) Int. Cl.[7] .............................................. A61C 15/00
(52) U.S. Cl. ........................ 132/321; 206/368; D28/65
(58) Field of Search ................................ 132/321, 322, 132/328, 329; 206/38, 368, 370, 63.5, 37, 380, 382; D3/273, 274; D28/65; 279/7, 202

(56) References Cited

U.S. PATENT DOCUMENTS

| | | | | |
|---|---|---|---|---|
| 2,072,777 A | * | 3/1937 | Takahashi | 30/123 |
| 2,488,535 A | * | 11/1949 | Hamburg | 118/500 |
| 3,042,191 A | * | 7/1962 | Riche | 206/96 |
| 3,216,124 A | * | 11/1965 | Goff | 33/199 R |
| 4,304,245 A | * | 12/1981 | Lichfield | 132/321 |
| 4,509,541 A | * | 4/1985 | Manciocchi, Jr. | 132/322 |
| 5,069,209 A | * | 12/1991 | Posin | 607/37 |
| 5,386,840 A | * | 2/1995 | Lane | 132/329 |
| 5,700,146 A | * | 12/1997 | Kucar | 433/82 |
| 6,418,940 B1 | * | 7/2002 | Tcherny et al. | 132/321 |
| 2003/0159709 A1 | * | 8/2003 | Brattesani et al. | 132/281 |

FOREIGN PATENT DOCUMENTS

| | | | |
|---|---|---|---|
| CH | 686336 A5 | * 3/1996 | |
| DE | 29610773 U1 | * 10/1996 | |
| DE | 19834247 A1 | * 2/2000 | |
| JP | 403173591 A | * 7/1991 | |
| JP | 404348717 A | * 12/1992 | 132/328 |

* cited by examiner

Primary Examiner—Todd E. Manahan
(74) Attorney, Agent, or Firm—Donald R. Boys

(57) ABSTRACT

An ornamental toothpick system has a toothpick and an ornamental extension having a body with an outer surface comprising one or more of a specular finish, ornamental indicia or text, and an engagement interface engaging the ornamental extension to the toothpick.

6 Claims, 4 Drawing Sheets

US 6,848,453 B2

ORNAMENTAL AND UTILITARIAN TOOTHPICK EXTENSION

FIELD OF THE INVENTION

The present invention is in the field of jewelry which is both ornamental and functional, and pertains more particularly to an extension for a conventional toothpick.

BACKGROUND OF THE INVENTION

It is well-known that many persons form habits involved with various articles and devices. One such is in regard to the use of toothpicks. Although conventional toothpicks are generally intended for use to pick unwanted matter from between a person's teeth, many persons have developed a habit of carrying such a toothpick in the mouth, held between the teeth or lips, or both.

It is equally well known that many persons enjoy displaying a personal taste for certain decorative artifacts. Many men now wear earrings, for example. Posts and rings are also now common for display on many areas of the body, which areas may be pierced, just as ear lobes have been pierced for many years in the past. It is well known, as well, that the use of such personal ornaments is very common among such as sports and music celebrities. Many NBA stars, for example, sport expensive earrings, often with diamonds and the like.

It has occurred to the present inventor that the common use of toothpicks might provide a further basis for personal ornamentation, and at the same time provide an opportunity for personal hygiene as well.

SUMMARY OF THE INVENTION

In a preferred embodiment of the present invention an ornamental toothpick extension is provided, comprising a body having an outer surface comprising one or more of a specular finish, ornamental indicia or text, and an engagement interface for engaging the ornamental extension to a toothpick. In some embodiments the extension further comprises a precious or semi-precious metal or one or more jewels, precious stones or pearls. Also in some embodiments the extension a lighting element with a power source such that light may be emitted from a portion of the extension.

In some other embodiments of the extension there is also a reservoir for one or more of hygienic, flavorful, or aromatic material, and the reservoir may have an interface for a toothpick, positioned such that the toothpick, assembled to the extension, penetrates (passes through) the interface.

In another aspect of the invention an ornamental toothpick system is provided, comprising a toothpick, and an ornamental extension having a body with an outer surface comprising one or more of a specular finish, ornamental indicia or text, and an engagement interface engaging the ornamental extension to the toothpick.

In some embodiments of the system the extension further comprises a precious or semi-precious metal or one or more jewels, precious stones or pearls. Also in some embodiments of the system the extension further comprises a lighting element with a power source such that light may be emitted from a portion of the extension. In still other embodiments the extension further comprises a reservoir for one or more of hygienic, flavor ful or aromatic material. The reservoir may further comprise an interface for a toothpick, positioned such that the toothpick, assembled to the extension, penetrates (passes through) the interface, and in some cases the toothpick may have a lengthwise capillary for conducting the hygienic or aromatic material from the reservoir through the toothpick.

BRIEF DESCRIPTION OF THE DRAWING FIGURES

DESCRIPTION OF THE PREFERRED EMBODIMENTS

Figure 1:
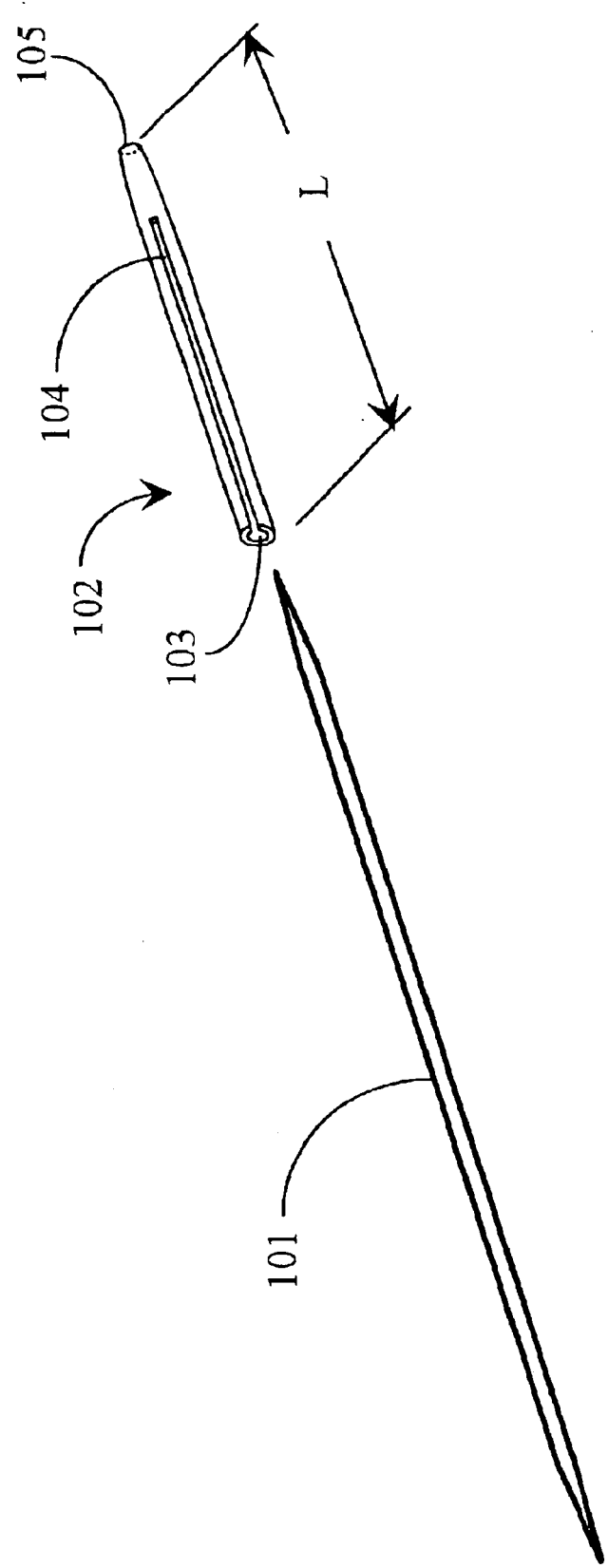
FIG. 1 is a perspective view of a conventional toothpick together with an adapter/ornamental extension according to a preferred embodiment of the present invention.

FIG. 1 is a perspective view of a conventional toothpick 101 together with an adapter/ornamental extension 102 according to a preferred embodiment of the present invention. Toothpick 101 is a conventional wooden toothpick as is well-known in the art, and may be encountered in the art in various diameters, lengths, tapers, and so forth. Typically such toothpicks are wooden, and are tapered to a point on at least one end, and sometimes on both ends. Such toothpicks are well known also in plastic, and may even be found in other materials.

Shown in-line with conventional toothpick 101 in FIG. 1 is an adapter/ornamental extension 102 with a hollow bore 103 of a diameter to slide over and engage the outer diameter of toothpick 101. Element 102 in some embodiments is an adapter for engaging toothpick 101 and for to providing an interface to add a separate ornamental and/or functional extension as taught further below. In another embodiment element 102 is itself an ornamental and/or functional extension for toothpick 101, to engage to the toothpick by sliding over the outer diameter of the toothpick.

In the embodiment shown element 102 has a slot 104 through the outer wall on one side only for a substantial portion of the length of the element. This slot has several functions. One function is to provide some diametrical spring expansion and contraction for sure engagement to toothpick 101. The inner diameter of bore 103, for example, may be just slightly smaller than the outer diameter of the toothpick, such that the sidewalls of element 102 have to expand slightly for bore 103 to slide over toothpick 101. The spring-like function as a result of slot 104 will ensure a quite sturdy engagement, with the sidewalls of element 102 urging into the outer diameter of the toothpick.

In some cases there may further be protrusions from inner walls of element 102 in bore 103 to further aid in retaining element 102 when engaged with a conventional toothpick.

Such protrusions may be angled in a manner that engagement with the toothpick is facilitated while disengagement is discouraged. In an alternative embodiment inner bore 103 may be provided with a spiral threaded topology, with perhaps a long pitch, so the toothpick may be engaged by relative rotation of the toothpick in bore 103.

Slot 104 also provides for facility in removing a toothpick from bore 103 so a new pick may be inserted, and an opening to facilitate cleaning of the bore 103. To further facilitate cleaning and the like, end 105 may be open, such that bore 103 essentially passes through the entire length of element 102. The length of element 102 may vary considerably in different embodiments, from nearly as long as toothpick 101, to only a fraction of the length of toothpick 101.

Adapter element 102 may be made of any one of several metals, such as stainless steel, copper, bronze, brass, steel, and so forth. It may also be made of any one of several plastics. It could even be made of wood or other material, as long as it performs the functions for which it is intended.

In some embodiments element 102 is itself ornamental, and may be then made of a precious metal, and may be integrated with jewels, and personal and/or ornamental indicia, such as fluting and the like. Techniques may also be applied for making a specular finish on the ornamental extension, such as gold plating, chrome plating, anodizing, and any one of many other techniques for providing an attractive finish. Names of individuals may be added as indicia, and other textual or ornamental indicia may be added as well. There are many, many ways that ornamentation and indicia may be added, and some of these are taught in more detail below, with reference to further figures in the present case.

Figure 2:
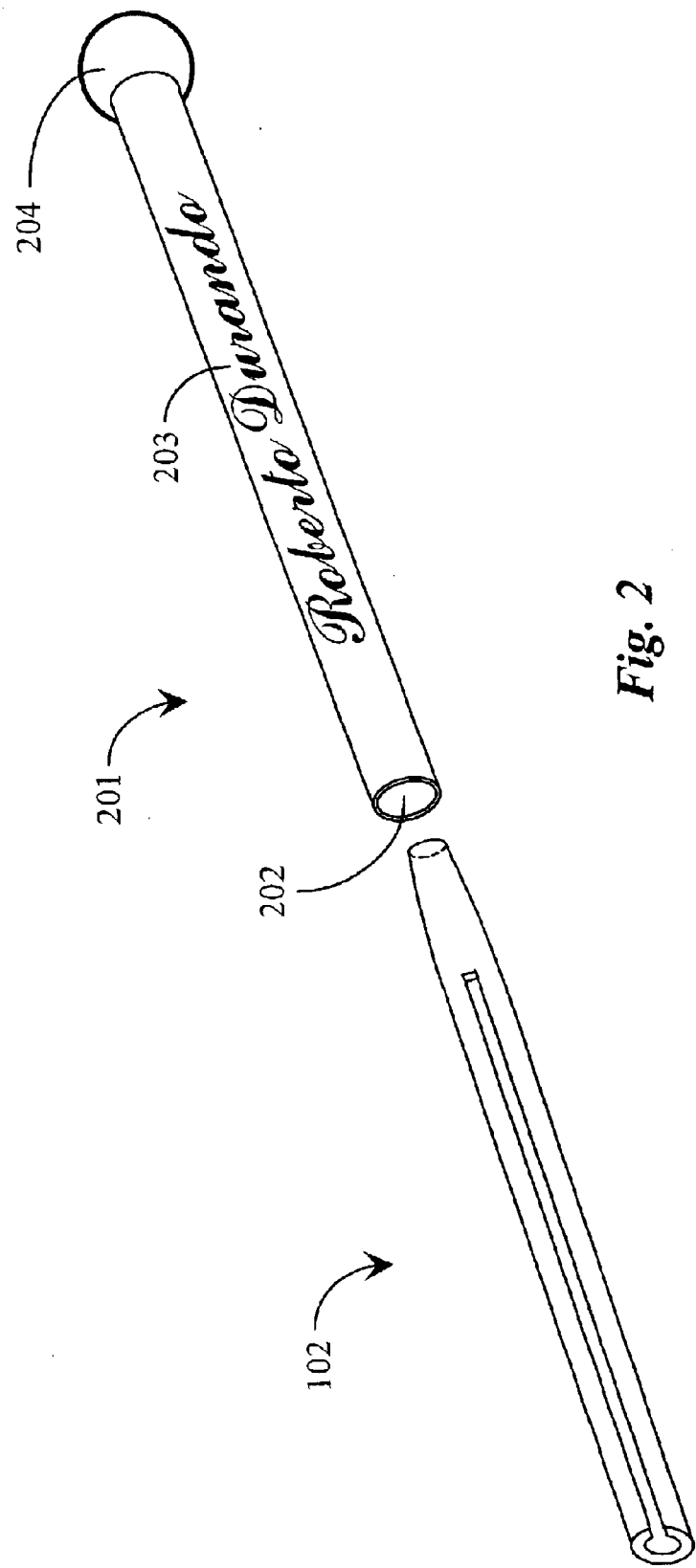
FIG. 2 is a perspective view of an ornamental toothpick extension shown with an adapter for a toothpick in an embodiment of the present invention.

FIG. 2 is a perspective view of an ornamental toothpick extension 201 shown with an adapter 102 for a toothpick in an embodiment of the present invention. Extension 201 in this embodiment is provided as an ornamental and, in some cases personalized accessory for an individual to use in lieu of just carrying a toothpick in the mouth. Adapter element 102 is described in some detail above, with reference to FIG. 1, and in the embodiment described here with reference to FIG. 2 is an adapter between a toothpick (101 of FIG. 1) and an ornamental extension 201 as shown in FIG. 2.

Extension 201 may comprise one or more precious metals, such as gold, silver, platinum and the like, in various combinations. There may also be ornamental indicia such as personalized text and designs upon the outer surface of extension 201. Techniques may also be applied for making a specular finish on the ornamental extension, such as gold plating, chrome plating, anodizing, and any one of many other techniques for providing an attractive finish. A person's name is shown in this example as element 203. Element 204 may be a jewel or a pearl or the like, and jewels and the like may be used elsewhere on such an extension as well. In a preferred embodiment bore 202 in extension 201 is made to allow a firm fit over the outside diameter of adapter 102, and the wall thickness of extension 201 may be quite thin to save the cost of precious ingredients, with bulk and strength made up by underlying adapter 102. In some cases, as described above, an ornamental extension 201 may be used without an adapter, and will then be designed to fit directly to the toothpick.

Figure 3:
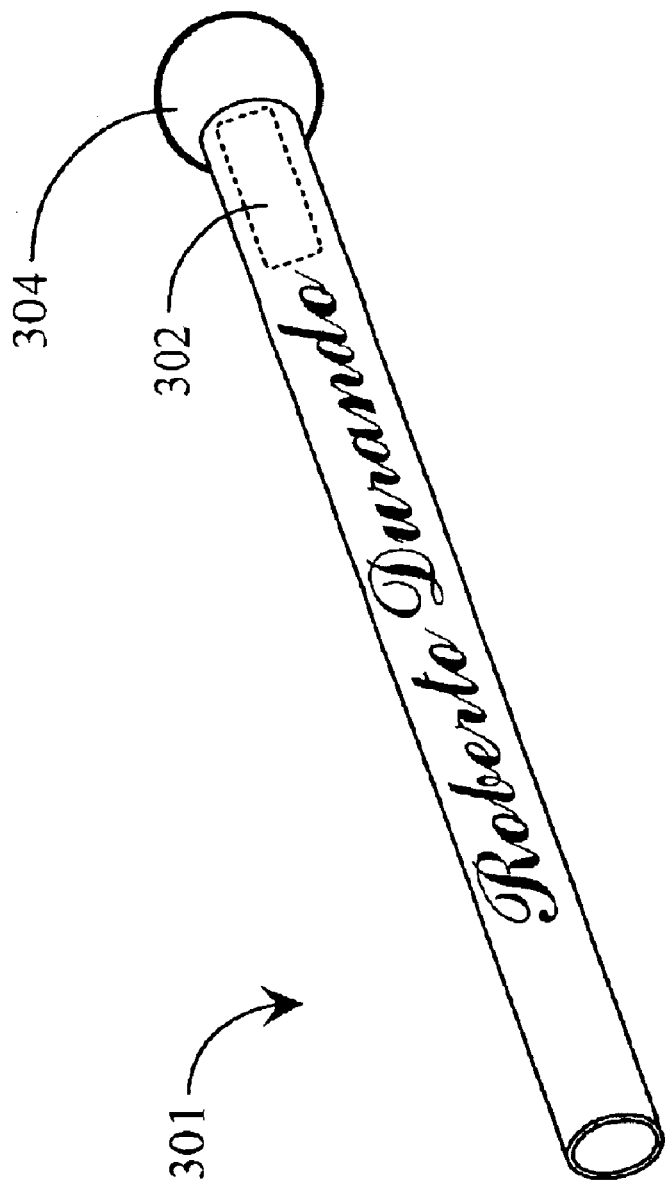
FIG. 3 is a perspective view of an ornamental toothpick extension in alternative embodiments of the invention.

FIG. 3 is a perspective view of an ornamental toothpick extension 301 in an alternative embodiment of the invention. In this example, element 304 may be a laser emitter or a light diffuser, or the like, and element 302 is a power source, such as a battery. In some embodiments the power source may be activated by inserting either a toothpick or an adapter for a toothpick. If element 304 includes an outer sheath of color, or even a translucent jewel, then a light source behind the jewel or sheath, such as a filament or a laser, when activated will cause the sheath or jewel to glow, providing an interesting effect in a darkened environment.

In another alternative embodiment a reservoir may be provided, and may be represented as well by element 302 in FIG. 3, the reservoir containing such as hygienic, flavorful and/or aromatic components (mouthwash). In this case, use of the ornamented toothpick can contribute to oral hygiene and fight tooth decay and bad breath, for example, depending on the material introduced from the reservoir. In some cases the material may have a flavor, such as mint, for example, to render the use more pleasant for the user. In some cases a toothpick may be used having a hollow lengthwise capillary down the center, completely through the length of the toothpick, to conduct material from a reservoir in the extension into a user's mouth, as described below for FIG. 4.

Figure 4:
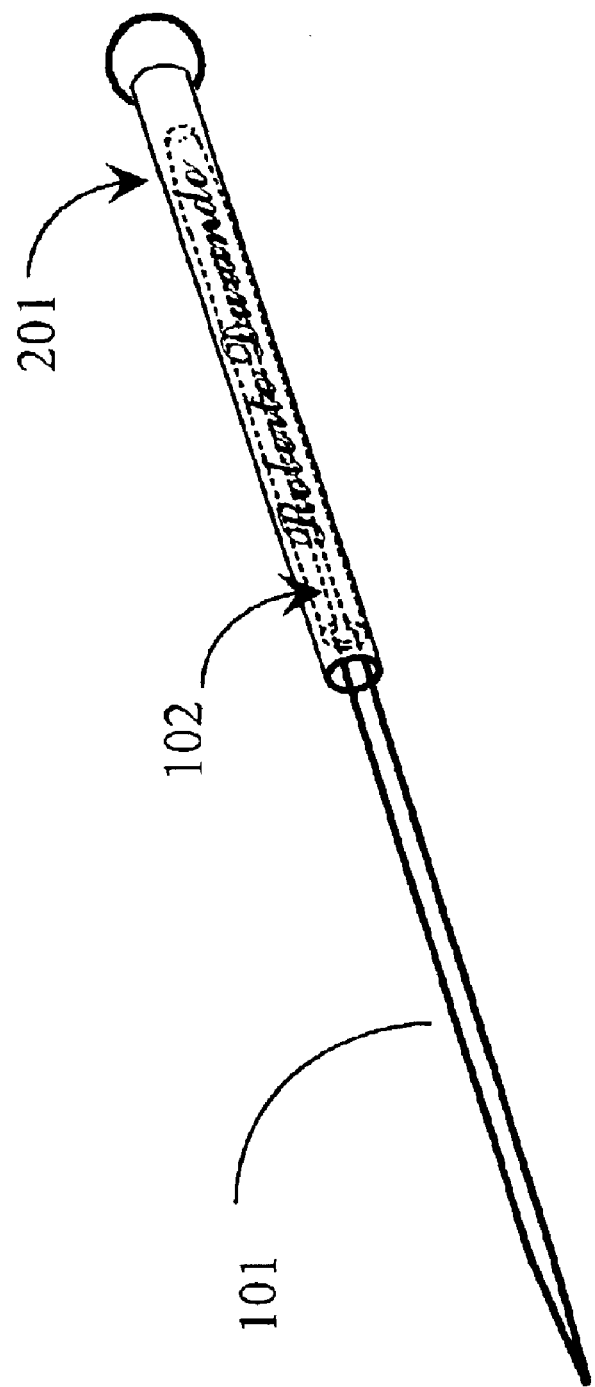
FIG. 4 is a perspective view of a conventional toothpick with an adapter and an ornamental extension engaged.

FIG. 4 is a perspective view of a conventional toothpick with an adapter and an ornamental extension engaged. This figure is provided to illustrate how the toothpick 101, the adapter 102 (shown in outline, as it is covered in this view by the extension) and the extension 201 are assembled together for use. Typically one takes a clean, new toothpick 101, which may be a unique toothpick, such as toothpick 101 having a capillary, said capillary illustrated as element 202 (also shown in outline), or a standard conventional toothpick, engages adapter 102, and then engages extension 201 over the adapter. The assembly is then ready for use, and the user simply inserts it into the mouth like a conventional toothpick. Dis-assembly is the opposite order of steps. One may also choose to wash and perhaps sterilize the dis-assembled components before reuse, selecting, of course, a new toothpick as well. In the case of utilizing a toothpick with capillary, adapter 201 also shows in a hidden view, reservoir 302 as described in FIG. 3 above. Reservoir 302 comprises an interface 203 for a toothpick such as 101 shown with capillary 202, positioned such that the toothpick, assembled to the adapter, passes through the interface, allowing the contents of reservoir 302 to flow out interface 203 and through the entire length of toothpick 101, via capillary 202, and exit an opening at the tip end of toothpick 101 into the user's mouth.

In summary, the invention in its several embodiments taught herein in enabling detail, and in other embodiments suggested to those with skill in the art by the teachings herein, provides a new personalized article for use by those who are inclined to carry a toothpick in the mouth, and also are inclined to personal, decorative articles. There may be many alterations made to the embodiments described without departing from the spirit and scope of the invention, as there are many ways in which one may personalize and decorate such an article, and the invention should be afforded the breadth of the claims below.

What is claimed is:

1. An ornamental toothpick extension apparatus, comprising:
   a toothpick interface adapter having a cylindrical body with an outer surface, and a hollow bore extending substantially along the length of the body;
   a slot through one side of the body of the toothpick interface adapter extending substantially along the length of the body; and
   a toothpick extension cover having a cylindrical body and an outer surface, and a hollow bore extending substantially along the length of the body;
   characterized in that the hollow bore of the toothpick interface adapter is of a diameter to slide over and engage the outer surface of a toothpick, and further characterized in that the hollow bore of the toothpick extension cover is of a diameter to slide over and engage the outer surface of the toothpick interface adapter.

2. The ornamental toothpick extension apparatus of claim 1 wherein the outer surfaces of the toothpick interface adapter and extension cover comprise one or more of a specular finish, ornamental indicia or text.

3. The ornamental toothpick extension apparatus of claim 1 wherein the toothpick interface adapter and extension cover further comprise a precious or semi-precious metal or one or more jewels, precious stones or pearls.

4. The ornamental toothpick extension apparatus of claim 1 wherein the extension cover further comprises a lighting element with a power source such that light may be emitted from a portion of the extension cover.

5. The ornamental toothpick extension apparatus of claim 1 wherein the extension cover further comprises a reservoir for one or more of hygienic, flavorful or aromatic material.

6. The ornamental toothpick extension apparatus of claim 5 wherein the reservoir further comprises an interface for a toothpick, positioned such that the toothpick, assembled to the extension, passes through the interface.

* * * * *